United States Patent [19]
Gehring et al.

[11] Patent Number: 5,625,051
[45] Date of Patent: Apr. 29, 1997

[54] NUCLEIC ACID STRUCTURE WITH PROTONATED CYTOSINE-CYTOSINE BASE PAIRS AND ITS USES

[75] Inventors: Kalle Gehring; Maurice Gueron, both of Paris; Jean-Louis Leroy, Antony, all of France

[73] Assignee: Ecole Polytechnique, Palaiseu Cedex, France

[21] Appl. No.: 535,379

[22] Filed: Sep. 28, 1995

Related U.S. Application Data

[63] Continuation of Ser. No. 121,200, Sep. 15, 1993, abandoned.
[51] Int. Cl.⁶ .................................................. C07H 21/00
[52] U.S. Cl. ............................................................ 536/24.2
[58] Field of Search ...................... 536/24.1, 24.2, 536/24.5

[56] References Cited

PUBLICATIONS

Uhlmann et al (1990) Chem. Rev. 90(4), 543–584.
Milligan et al. (1993) J. Med. Chem, 36(14), 1923–1937.
Leroy et al. (1993) Biochem. 32, 6019–6031.

*Primary Examiner*—George C. Elliott
*Attorney, Agent, or Firm*—Burns, Doane, Swecker & Mathis, L.L.P.

[57] ABSTRACT

An 'i-motif' nucleic acid, DNA and/or RNA, complex characterized by the presence of at least four cytosine-rich stretches or stretches rich in cytosine derivatives, including two parallel-stranded duplexes in which the cytosines or derivatives thereof form base pairs, said two duplexes being associated anti-parallel to one another, and said pairs of cytosine or derivatives thereof of one duplex being intercalated with those of the other duplex.

17 Claims, 4 Drawing Sheets

5,625,051

NUCLEIC ACID STRUCTURE WITH PROTONATED CYTOSINE-CYTOSINE BASE PAIRS AND ITS USES

This application is a continuation, of application Ser. No. 08/121,200, filed Sep. 15, 1993, abandoned.

FIELD OF THE INVENTION

This invention concerns a new nucleic acid structure and its applications. The present invention is based on the demonstration of a new mode of association of nucleic acids, particularly those involving sequences of cytosines. The subject invention has many important applications, e.g., for the understanding of genetic mechanisms, controlling gene expression, for targeting of desired compounds to specific DNA's, for purification of compounds, etc.

BACKGROUND OF THE INVENTION

Until fairly recently, most research and applications relating to DNA have been concerned with the conventional Watson-Crick structure wherein two helical polynucleotide strands form a duplex because of hydrogen bonding between the bases on one strand to those of the other strand to form the purine-to-pyrimidine base pairs, AT and GC.

It has been known for some time that the polynucleotide polydT will bind to the polydA-polydT duplex to form a collinear triplex (Arnott, S & Selsing E. (1974) J. Molec. Biol. 88, 509). The structure of that triplex has been deduced from X-ray fiber diffraction analysis and has been determined to be a collinear triplex (Arnott, S. & Selsing E. (1974) J. Molec. Biol. 88, 509). The polydT strand is bound in the parallel orientation to the polydA strand of the underlying duplex. The polydT-polydA-polydT triplex is stabilized by T-A Hoogstein base pairing between A in the duplex and the third strand of polydT. That interaction necessarily places the third strand, called a ligand, within the major groove of the underlying duplex. The binding site in the major groove is also referred to as the target sequence.

Similarly, it has been shown that polydG will bind by triplex formation to the duplex polyG-polydC, presumably by G—G pairing in the major helix groove of the underlying duplex, (Riley M., Mailing B. & Chamberlin M. (1966) J. Molec. Biol. 20, 359). This pattern of association is likely to be similar to the pattern of G-G-C triplet formation seen in tRNA crystals (Cantor C. & Schimmel P., (1980) Biophysical Chemistry vol. I, p. 192-195).

Triplexes of the form polydA-polydA-polydT and polydC-polydG-polydC have also been detected (Broitman S., Im D. D. & Fresco J. R. (1987) Proc. Nat. Acad. Sci U.S.A. 84, 5120 and Lee J. S., Johnson D. A. & Morgan A. R. (1979) Nucl. Acids Res. 6, 3073). Further the mixed triplex polydCT-polydGA-polydCT has also been observed. (Parseuth D. et al. (1988) Proc. Nat. Acad Sci. U.S.A. 85, 1849 and Moser H. E. & Dervan P. B. (1987) Science 238,645). These complexes, however, have proven to be weak or to occur only at acid PH.

Parallel deoxyribo oligonucleotide isomers which bind in the parallel orientation have been synthesized (Moser H. E. & Dervan P. E. (1987) Science 238, 645–650 and Rajagopol P. & Feigon J. (1989) Nature 339, 637–640). In examples where the binding site was symmetric and could have formed either the parallel or antiparallel triplex (oligodT binding to an oligodA-oligodT duplex target), the resulting triplex formed in the parallel orientation (Moser H. E. & Dervan P. E. (1987) Science 238, 645–650 and Praseuth D. et al (1988) PNAS 85, 1349–1353), as had been deduced from x-ray diffraction analysis of the polydT-polydA-polydT triplex.

Studies employing oligonucleotides comprising the unnatural alpha anomer of the nucleotide subunit, have shown that an antiparallel triplex can form (Praseuth D. et al. (1988) PNAS 85, 13449–1353). However, since the alpha deoxyribonucleotide units of DNA are inherently reversed with respect to the natural beta subunits, an antiparallel triplex formed by alpha oligonucleotides necessarily follows from the observation of parallel triplex formation by the natural beta oligonucleotides. For example, alpha deoxyribo oligonucleotides form parallel rather than antiparallel Watson-Crick helices with a complementary strand of the beta DNA isomer.

It has been demonstrated that a DNA oligonucleotide could bind by triplex formation to a duplex DNA target in a gene control region; thereby repressing transcription initiation (Cooney M. et al. (1988) Science 241, 456). This was an important observation since the duplex DNA target was not a simple repeating sequence.

U.S. Pat. No. 5,176,996 issued on Jan. 5, 1993 to Hogan et al. discloses a method for making synthetic oligonucleotides which bind to target sequences in a duplex DNA forming collinear triplexes by binding to the major groove. This method includes scanning genomic duplex DNA and identifying nucleotide target sequences of greater than about 20 nucleotides having either about at least 65% purine bases or about 65% pyrimidine bases; and synthesizing synthetic oligonucleotides complementary to identified target sequences. The synthetic oligonucleotides have a T when the complementary location in the DNA duplex has a GC pair and have a 7 when the complementary location in the DNA duplex has an AT basepair. These synthetic oligonucleotides are oriented 5' to 3' and bind parallel or 3' to 5' and bind antiparallel to the about at least 65% purine strand.

DNA triple helices have been reported in the literature to have applications in inhibiting and regulating the function of targeted genes. For example, McShan et al, J. Biol. Chem., 267, 5712, (1992), reported that mixed purine-pyrimidine oligodeoxyribonucleotides designed to form collinear DNA triplexes with purine-rich elements in the HIV-1 promoter inhibit the transcription of HIV-1 in infected human cells.

Also, Postel et al, Proc. Nat'l Acad. Sci., 88, 8227, (1991) reported a triplex-forming oligonucleotide which binds to the C-myc promoter in HeLa cells and inhibits the transcription of C-myc mRNA. Further, Weiss et al, Abstract, Int. Conf. on Nucl. Acid Med. Appl., Abstract 4–34, demonstrate that a 26mer designed to form a triple helix with an interferon inducible gene caused a reduction in gene expression from HeLa cells, keratinocytes, corneal cells and retinal pigmented endothelial cells in a dose dependent manner at micromolar concentrations. However, there still exists a need in the art for polynucleotide sequences having unique structures and properties.

SUMMARY OF THE INVENTION

It is an object of the invention to provide a novel nucleic acid structure having superior properties, e.g., a high degree of thermostability.

It is a specific object of the invention to provide novel tetrameric nucleic acid structures or polynucleotide precursors which may be used to obtain such novel tetrameric nucleic acid structures.

It is a more specific object of the invention to provide an "i-motif" nucleic acid structure comprising a DNA and/or RNA containing complex characterized by the presence of at least four cytosine-rich stretches or stretches rich in cytosine derivatives having two parallel-stranded duplexes in which the cytosine or cytosine derivatives form basepairs and said duplexes are associated anti-parallel to one another and wherein said pairs of cytosine or cytosine derivatives comprised in one duplex are intercalated with those of the second duplex.

It is another specific object of the invention to provide nucleic acid sequences which comprise two or more consecutive cytosines which have a structure which permits them to associate with a nucleic acid having a similar structure to form an "i-motif".

It is another object of the invention to provide affinity chromatography columns which comprise an "i-motif" nucleic acid structure or a nucleic acid sequence which comprises stretches of two or more consecutive cytosines and which is designed to associate with a similar nucleic acid sequence by formation of an "i-motif".

It is another object of the invention to use an affinity column comprising an "i-motif" nucleic acid structure or a nucleic acid sequence which may be used to produce a nucleic acid sequence having an "i-motif" structure to isolate compounds which interact with "i-motif" nucleic acid structures.

It is another object of the invention to target a DNA or non-DNA type compound to a cytosine-rich sequence of a desired DNA by attaching said compound to a DNA sequence having a cytosine-rich stretch and contacting the resulting compound with a cytosine-rich stretch containing DNA under conditions which provide for the formation of a stable nucleic acid "i-motif" complex, e.g., acidic conditions.

It is another object of the invention to induce the formation of an "i-motif" complex by treating at least one nucleic acid sequence having at least two cytosine-rich sequences under conditions which promote the formation of a stable "i-motif" structure, e.g., the use of an acidic medium.

It is yet another object of the invention to use the subject novel "i-motif" nucleic acid structures in novel intercalation processes, and for regulating gene expression, in both sense and antisense strategies involving the "i-motif". Such methods may be used to inhibit cell growth, alter protein ratios, treat diseases such as cancer, or to alter a particular nucleic acid structure.

It is another object of the invention to use the "i-motif" as a component of a supramolecular scaffold which may carry and organize groups with catalytic or electronic properties, e.g., for use in vitro and in vivo for chemical and enzymatic probing and measurement, for computational analysis and processing of the latter, and for the generation of elements of molecular memorization and computing.

BRIEF DESCRIPTION OF THE PREFERRED EMBODIMENTS

The present invention concerns an "i-motif" nucleic acid, DNA and/or RNA containing complex characterized by the presence of at least four cytosine-rich stretches or stretches rich in cytosine derivatives, including two parallel-stranded duplexes in which the cytosines or derivatives thereof form base pairs, said two duplexes being associated anti-parallel to one another, and wherein said pairs of cytosine or derivatives thereof of one duplex are intercalated with those of the other duplex.

Such a structure has been specifically demonstrated by nuclear magnetic resonance (NMR) in the case of the oligomer 5'-d(TCCCCC). However, the invention is applicable to any cytosine-rich oligomer which results in the subject "i-motif" structure under appropriate conditions.

In order to understand the structure of the "i-motif", it must be emphasized that the structure of each of its constituent parallel-stranded duplexes differs from that of the usual DNA duplex because the base pairing scheme involves hemiprotonated cytosines which result in the formation of C.C+ base pairs. This can be more clearly seen in FIG. 1.

Figure 1:
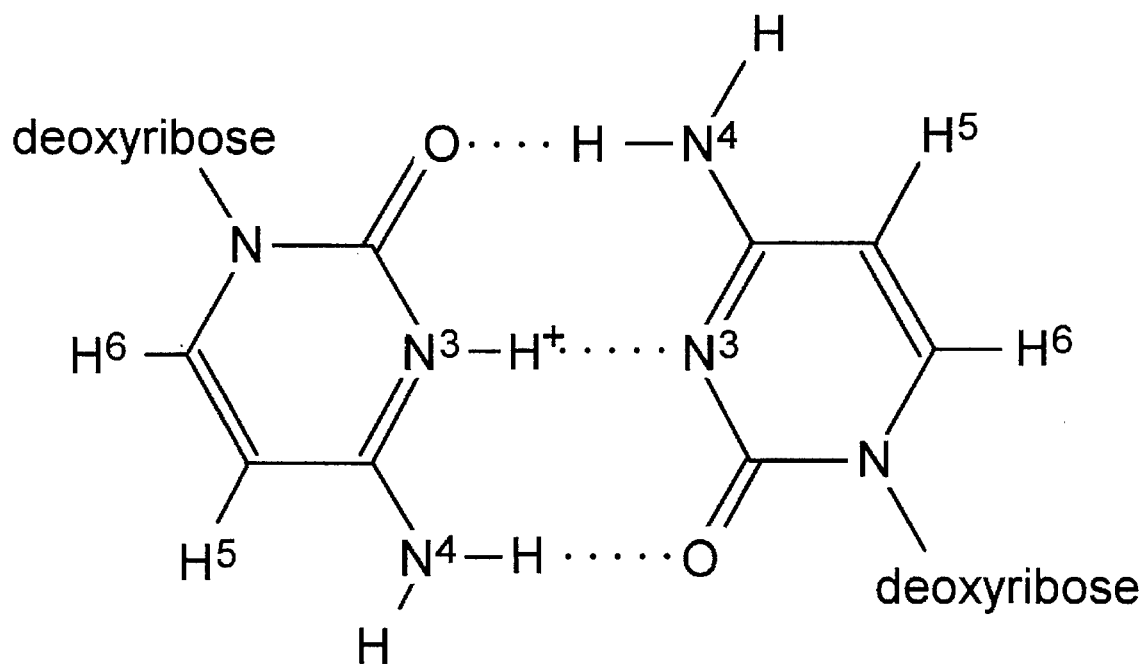
FIG. 1 This figure depicts the scheme of hydrogen bonding in cytosine-protonated cytosine (C.C+) base pairs.

Specifically, FIG. 1 displays the interactions occurring between cytosines pairs, of which one of said cytosines contained in each pair is protonated. It is also within the scope of the present invention to provide for the same interactions using derivatives of cytosine which comprise chemical substitutions that enable said cytosine base-pairing scheme to be maintained. Moreover, some of such cytosine derivatives may be advantageous since they may provide for the formation of more stable "i-motif" structures.

Figure 2:
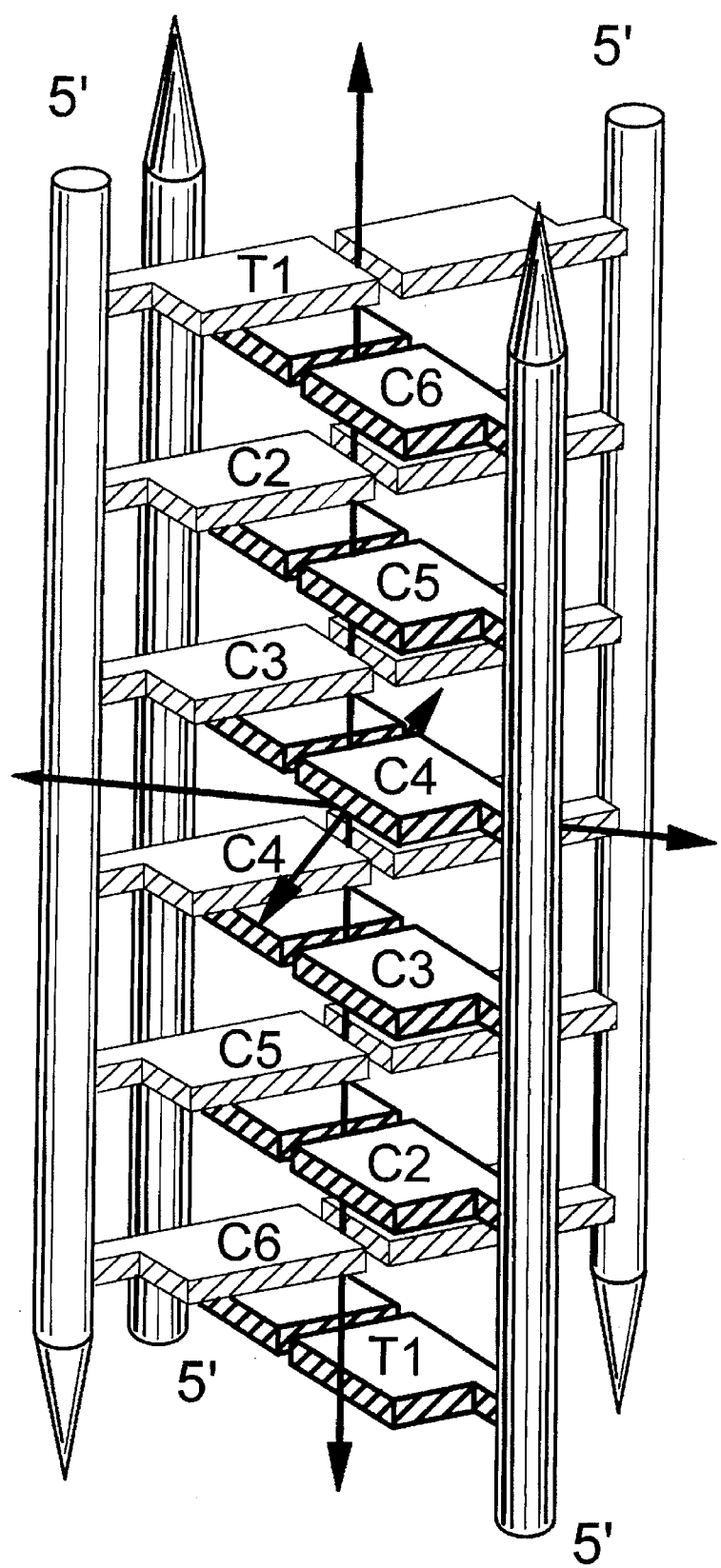
FIG. 2 This figure depicts the proposed model of the d(TC$_5$) tetrad and the intercalation scheme of the two parallel duplexes.

The "i-motif" may exist as a tetramer formed by the association of two duplexes as described above. Such a structure is represented in FIG. 2 wherein the white and the black duplexes are oriented anti-parallel to one another, with intercalated cytosine base pairs. This structure contains three axes of 2-fold symmetry (arrows): one along the helix axis through the center of each C.C+ base pair, and two between the central C4.C4 base pairs. It is further noted the terminal thymidines in the structure may or not be base-paired.

The above-described intercalated structure which involves cytosines or derivatives has been named by the inventors and is referred to throughout this application as the "i-motif" structure.

The above-described structure described corresponds to a specific oligomer, under given conditions. However, similar structures may be obtained for oligomers containing derivatives of cytosine, such as 5-methylcytosine, rather than cytosine, or with other derivatives of cytosine. The identification of suitable cytosine derivatives which provide for the subject "i-motif" structure is within the level of skill in the art. The development of such DNA or RNA oligomers has many important applications, especially in sense or antisense strategies, involving the regulation of altering particular genes.

The complex described here is preferably synthesized from sequences including a stretch of at least two consecutive cytosines, or more preferably four. When more cytosines contribute to the "i-motif", the stability of the motif is increased. However, it is not required that all cytosines in a stretch contribute to the "i-motif". Moreover, this motif may be formed by the interaction of stretches containing different numbers of cytosines. Furthermore, a cytosine-rich stretch may contain one or two non-cytosine base(s) in between the cytosines. However, this may reduce the stability of the "i-motif".

The complex described herein is stable in slightly acidic conditions, preferably at a pH less than 6.8. However, stable complexes may be obtained by alternative methods, e.g., by altering the composition of the solution, or by using specific derivatives of cytosine and/or by using stabilizing flanking sequences next to the stretches of cytosine. It is particularly desirable that the complex or parts thereof are produced from polymers which differ from natural nucleic acids, for example, nucleic acids wherein the sugar-phosphate part has been modified by substitution or insertion of chemical groups so as to provide novel properties to the complex, such as higher chemical in vivo and/or in vitro stability.

The four cytosine stretches which comprise the "i-motif" may belong to different strands of nucleic acids, however, any two of them may also be linked together covalently. Also, any two of them may be part of a single nucleic acid strand wherein they are separated by a stretch of specified bases.

In order to produce the "i-motif" complex of the present invention, it is necessary to obtain nucleic acid sequences containing the requisite cytosine-rich regions. For example, one may synthesize nucleic acid strands which carry at least two stretches of cytosines according to known methods of nucleic acid synthesis. Two of such strands are then connected by base pairs involved in an "i-motif" in such a way that each strand is folded into a hairpin structure. However, it is also possible, as shown in the examples below, to build the "i-motif" upon a single strand containing four cytosine stretches. This is the case, for instance, with the sequence $C_4A_2C_4A_2C_4A_2C_4$, which can fold upon itself to form an "i-motif" including eight cytosine—protonated cytosine base pairs.

Of course, if the cytosine-rich region which generates the "i-motif" includes a non-cytosine base, one may encounter situations where this base intercalates within the "i-motif". However, if the cytosine-rich stretch is long enough, this should not destroy the "i-motif".

Given its unique structure, the present complex comprises a remarkably high thermodynamical stability. This is due in part to its novel scheme of intercalation.

There are many differences which distinguish the subject "i-motif" from conventional polynucleotide structures, most particularly its tetrameric structure. Another important difference of the subject "i-motif" which distinguishes it from conventional DNA structures is that the intercalating elements are base pairs. A further difference is that intercalation occurs at every inter base-pair location. This is in contradiction to commonly observed intercalations in DNA, wherein the intercalator is not a base-pair, and in which there is de facto an "excluded site" rule by which intercalation at the locus between two base pairs is incompatible with simultaneous intercalation at a contiguous locus.

As a result of such properties, the present complex can be of use in the context of novel intercalation process, or in sense or antisense strategies involving the "i-motif".

The subject "i-motif" may also be used to target DNA or non-DNA compounds to a cytosine-rich region of a particular DNA. In particular, this may be effected by attaching a DNA or non-DNA compound to a DNA sequence having cytosine-rich regions and then contacting the resulting compound with a desired DNA containing a cytosine-rich region under conditions which provide for the formation of a stable "i-motif" complex, e.g., acidic conditions. This aspect of the invention has significant research potential for studying gene function and regulation as well as for therapeutic and diagnostic applications. For example, a detectable moiety may be targeted to a specified DNA according to such a method, e.g., a radionuclide, and then detected using known methods. Alternatively, a therapeutic compound may be targeted to a desired sequence, e.g., an alkylating agent. The potential of such methods are extremely exciting. Moreover, given the high stability of the subject "i-motif", the compound should be effectively retained at the desired targeted site.

The specific DNA may come from a natural DNA sequence, or may be produced by synthetic methods. Of course, it may be observed in the duplex form (Watson-Crick) under appropriate conditions.

Among the possible DNA compounds, the compound may be a DNA-type compound including a DNA sequence designed in view of a sense or antisense strategy, that is a strategy aimed to either inhibit or promote the activity of a given sequence. In the case of a non-DNA-type compound, the compound may exhibit a pharmacological activity such as that of an intercalator agent or of an alkylating agent or of other agents acting for instance on DNA itself.

In some cases, one may use directly the interaction with a specific cytosine-rich DNA sequence. The compound would then be a DNA segment with at least two cytosine-rich stretches, which is treated under conditions which favor the formation of the "i-motif", for instance in an acidic medium or other conditions otherwise favoring the stability of the "i-motif". The formation of an "i-motif" complex may be itself sufficient to alter the sense/antisense properties of the specific DNA molecule, e.g., a chromosomal DNA.

As specific examples of cytosine-rich sequences which could be the subject to such applications, we mention those which exist in telomeres and in centromeres.

The complex described in the present invention may be involved specifically in the properties displayed by such sequences, and by sequences tailored to specifically interact with them.

The subject "i-motif" complex is further to be used in processes for selecting compounds which interact with structures comprising or relating to the "i-motif" structure. These compounds may be isolated with an affinity chromatography column comprising an "i-motif" nucleic acid complex or an "i-motif" precursor which provides for the formation of "i-motif" structures under appropriate conditions, which associates "i-motif" with the desired compound. Such compounds will have pharmacological properties related to their affinity for the complex. Also, compounds which interact with "i-motif" and related structures may be selected not only by affinity chromatography as above, but also by related electrophoretic procedures.

Such an affinity chromatography column, will generally comprise a resin to which is attached an "i-motif" nucleic acid complex, or one of its precursors, and which may be used to identify and isolate compounds which bind with the "i-motif" structure.

The present invention also provides nucleic acid sequences which include stretches of two or more consecutive cytosines, which are designed such that they associate with a similar nucleic acid sequence by formation of an "i-motif" complex between the cytosine stretches. Thus, they function as precursors for the formation of an "i-motif" structure.

The invention also provides a process for inducing the formation of an "i-motif" complex comprising subjecting at least one nucleic acid segment having at least two cytosine-rich sequences to acidic conditions or other conditions which promote the formation of a stable "i-motif" complex.

Finally, the invention deals with a process wherein the "i-motif" is used as a component of a supramolecular scaffold which may carry and organize groups with catalytic or electronic properties in view of applications, in vitro or in vivo, to chemical or enzymatic probing and measurements, to the computation, analysis and processing of the latter, and to the generation of elements of molecular memorization and molecular computing.

Other properties and benefits of the present invention will be made apparent by the following examples:

EXAMPLE 1

The Structure and Stoichiometry of the Complex Formed by the Hexamer d(TC$_5$)

5'-d(TCCCCC) (10 μmol) is synthesized by standard phosphoramidite chemistry on a Pharmacia Gene Asseniber with a CPG resin (Millipore). After work-up and purification, the sample (200 optical density units as a Na+ salt) is dialyzed against distilled H$_2$O and the pH lowered to 4.3 with HCl. Occasionally, slow cooling is necessary to eliminate unwanted conformers.

The structure of the oligomer is analyzed by a two-dimensional NMR spectrum. Two-dimensional NMR spectrum is acquired at 25° C. on an AMX600 spectrometer (Bruker Spectrospin). Strand concentration is 7.5 mM.

The proton NMR spectrum of D(TC$_5$) in H$_2$O (90%), pH 4.9, −5° C., displays five imino proton resonances at 15 to 16 ppm with an integrated area of one proton per pair of cytidines with intensities of 0.5 (1,2,1, and 1) per strand, showing that all C.C+ base pairs are formed. The observation of these resonances is strong evidence of imino proton hydrogen-bonding.

The transition between the single-stranded and multi-stranded form can also be followed in the NMR spectrum of the non-exchangeable protons. The number of resonances in the single and multistranded forms is the same, which implies that all of the DNA strands in the multistranded form are identical on the NMR timescale.

As a matter of fact, the NMR spectrum displays only six spin systems, showing that the structure is highly symmetrical on the NMR timescale; the four strands are equivalent.

The sugar proton resonances of the multistranded acid form are assigned to one of the six nucleotide spin systems by COSY and TOCSY experiments using only through-bond J-coupling. The NOESY mixing time is 240 ms 240 ms with $^{31}$P-decoupling in the t2 dimension. The hereto-TOCSY used a DIPSI-2 mixing pulse sequence (6 loops, 35 ms) with 32 TPPI increments, 800 scans per increment and a 2-s recycle delay. Spectra are processed using FELIX 1.1 (Hare Research) with skewed sine-bell squared apodization functions, and plotted with a factor of 1.3 between contour levels.

These groupings are also found in the intraresidue NOEs (FIG. 3a), between the H6 base protons and the H3', H4', H5'/H5" protons. The H6 are assigned through these NOES.

The deoxyribose spin systems are aligned independently of any NOESY experiments by a heteronuclear $^1$H-$^{31}$P TOCSY experiment. In the spectrum, each phosphorus resonance shows crosspeaks with the H3' resonance of the preceding nucleotide and with its own H5' and H5" resonances (FIG. 3b).

Figure 3:
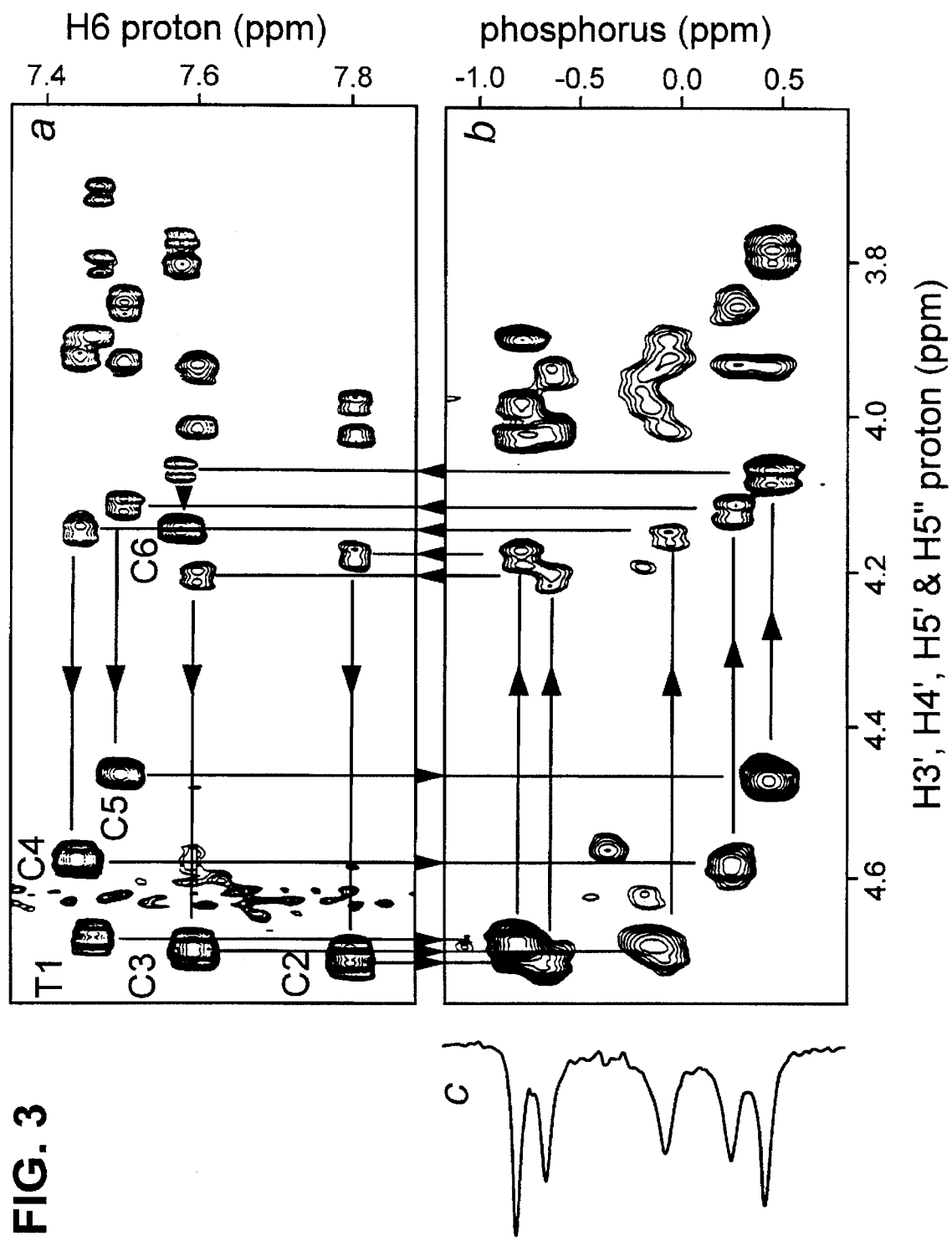
FIG. 3(a–c) This figure shows the assignment of the phosphorus and sugar proton resonances of d(TC$_5$) in a heteronuclear total correlation spectroscopy (tocsy) experiment.

FIG. 3c shows a one-dimensional 1H-decoupled phosphorus spectrum of the tetrad d(TC$_5$) 162 MHz, 2,048 scans, 3s recycle delay.

Figure 4:
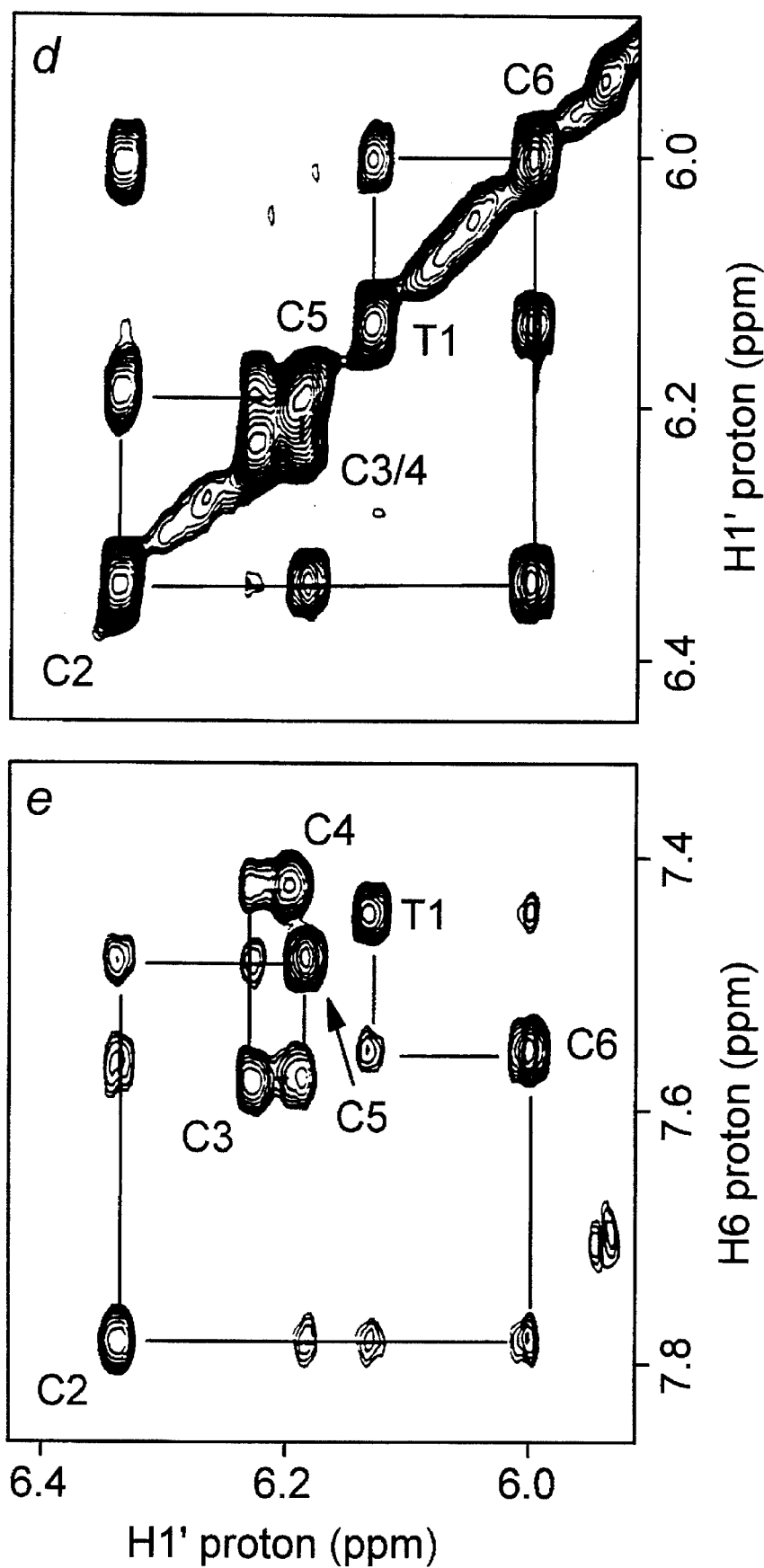
FIG. 4(d–e) This figure illustrates the determination of the order of base-pair stacking in the complex from NOESY spectra.

NOESY experiments at mixing times of 30 and 240 ms show very unusual inter-residue sugar-sugar NOEs (FIG. 4A, B; top). FIG. 4 shows the determination of the order of base-pair stacking in the complex from NOESY spectra at short (A, 30 ms) and long mixing times (B, 240 ms). The top portion of the figure shows the stacking order according to H1'-H1 pseudosequential NOE crosspeaks: T1-C6-C2-C5-C¾. The 30-ms spectrum emphasizes direct crosspeaks between proton at close distance. The lower portion shows H'7-H6 NOES. Lines connect the intra-residue (labelled by residue) and inter-residue H6-H1' pseudo-sequential NOEs to give the complete order of base-pair stacking: T1-C6-C2-C5-C3-C4. The equal intensity of the of H6-H1' (5' to 3') and H1'-H6crosspeaks is a consequence of the face-to-face orientation of the base pairs. There is one true sequential crosspeak between T1H1' and C2H6.

The assignment of the deoxyribose protons establishes that they are essentially all long-range NOEs (between residues distant in the primary sequence). Similar long-range NOEs are found in many regions of the NOESY spectra: imino—imino, imino-H6, H6-H3', H1'-H2", H1'-H4', H5-H1' and H6-H1'. In this last region, the sequence of NOEs can be read in its entirety as: T1-C6-C2-C5-C3-C4 (FIG. 4a).

Only the four-stranded model is consistent with both the C.C+ basepairing scheme and the observed equivalence of all the DNA strands.

A model derived by energy minimization and constrained molecular dynamics show excellent compatibility with the observed Nuclear Overhauser Effects (NOES) particularly for the very unusual inter-residue sugar—sugar NOEs H1' H1' H1'-H2" and H1'-H4'. These NOEs are probably diagnostic for such tetrameric structures.

Independent evidence for a tetrameric complex comes from dilution experiments using polyacrylamide gel electrophoresis as set forth below:

Serial twofold dilutions of D(TC$_5$) are mixed with a small amount of 5'-$^{32}$P-labelled D(TC$_5$) and allowed to equilibrate in (80 mM Tris-acetate, 1 mM EDTA, pH 4.5) at 10° C. before gel electrophoresis on a 20% non-denaturating polyacrylamide gel (run at 2° C. for 6 h at 10 V per cm). The relative proportions of radioactive decay in the T.D and M species in each lane are measured on a Molecular Dynamics Phosphorimager and the concentrations of each species calculated. Depending on the methods used for base-line correction and integration, the calculated stoichiometry (least-squares slope) varied between 3.5 and 4.0 for the T species alone, and between 3.2 and 3.5 when the D and T species were pooled. Gel electrophoresis at pH 8 shows only a single species at all concentrations.

At pH 4.5, the oligonucleotide d(TC$_5$) migrates in a non-denaturating gel as three species whose relative proportions are strongly concentration-dependent. At concentrations above 100 μM, a slowly migrating species (T) dominates; at intermediate concentrations, a more rapidly migrating species (D) appears, and at concentrations below I μM the most rapidly migrating species (M) dominates. At thermodynamic equilibrium (achieved by slow cooling before electrophoresis), the stoichiometry of the T species can be measured by plotting the logarithm of its concentration against that of the presumed monomer species (M). From the slope of a line of best fit, we conclude that the slowly migrating T species is a complex of four strands.

EXAMPLE 2

Stoichiometry, Base-Pair Characterization and Proton Exchange Properties of $d(C_{12})$, $d(T_2C_8T_2)$, $d(C_4TC_4)$, $d(TC_3)$, $d(C_4)$, $d(TC_4)$, $d(TC_3)$ AND $d(TC_3)$ The oligonucleotides are synthesized as described in example 1.

Proton exchange studies are performed in 0.1M NaCl solution with strand concentrations ranging from 1 to 6 mM.

For the NMR measurements, the multimers are usually prepared by lowering the pH of a solution at the final strand.

Acidification of the $d(C_4TC_4)$ oligonucleotide in this manner produced a gel. The acid form was therefore prepared from a dilute solution (strand concentration <0.1 mM) at pH 8. The solution was dialyzed at room temperature against water maintained at pH 5, lyophilized, and redissolved at 4° C. to the concentration of the 4MR experiment. Irreversible line broadening indicative of aggregation occurred at temperatures above 15° C.

The other cytidine strands studied here behave similarly to $d(TC_5)$ as regards the pH and temperature dependence of the single-strand to tetramer transition. The melting temperature is generally lower for shorter strands. Except for unresolved peaks and for exchange broadening, the imino proton spectrum contains one peak for each cytidine, with an intensity of 0.5 proton per base. Tetramer formation was studied in particular detail in $d(TC_3)$ and in $d(TC_2C_8T_2)$.

At a strand concentration of 4 mM, the tetramer of $d(TC_2C_8T_2)$ forms cooperatively around pH 6.5, and this value is nearly temperature-independent between 0° and 35° C. Experimental conditions are: pH 4.8, NaCl 100 mM, concentration in strands 5 mM. The chemical shift reference is DSS. At −5° C., the cytidine imino proton region, normalized to the thymidine imino proton peak, shows a cluster of seven nearly resolved NMR lines integrating to 3.5±0.3 protons and a line at 14.88 ppm of intensity 0.5±0.1 per single strand. This line, and no others, has an NOE connectivity with the imino proton peaks of thymidine (not shown). Each of the two amino proton clusters integrates to 8±1.5 protons, or a total of 1 per cytidine, as expected.

The stoichiometry of the $d(TC_3)$ complex is determined directly by NMR titration of the concentration-dependent equilibrium between the single-strand species whose NMR spectrum dominates at low concentration, and the complex with which it is in slow exchange, and which dominates at high concentration. From the intensity of a spectral feature (e.g. the peak of a methyl of T) of the complex and of the single strand, one obtains their concentrations. A log plot of the concentration of the complex versus that of the single strand has a slope of 4, thus establishing the stoichiometry of the complex and demonstrating that it is a tetramer.

We claim:

1. An isolated "i-motif" nucleic acid complex which comprises DNA and/or RNA which complex comprises at least four cytosine-rich regions or regions rich in cytosine derivatives and having two parallel-stranded duplexes in which the cytosine or cytosine derivatives form base pairs and wherein said duplexes are associated anti-parallel to one another and further wherein said pairs of cytosine or cytosine derivatives contained in one of said duplexes are intercalated with those of the second duplex.

2. The "i-motif" nucleic acid complex of claim 1 wherein each of said cytosine-rich regions comprise at least two consecutive cytosines or cytosine derivatives.

3. The "i-motif" nucleic acid complex of claim 1 which has been produced by treating one or more nucleic acid structures comprising cytosine-rich regions or regions rich in cytosine derivatives under acidic conditions.

4. The "i-motif" nucleic acid complex of claim 3 wherein said cytosine-rich regions each comprise at least two consecutive cytosines or cytosine analogs.

5. The complex of claim 1 which is produced from a single stranded nucleic acid molecule comprising at least four cytosine-rich or cytosine derivative-rich regions.

6. The complex of claim 2 which is produced from a single stranded nucleic acid molecule comprising at least four cytosine-rich or cytosine derivative-rich regions.

7. The complex of claim 1 wherein the cytosine-rich or cytosine derivative-rich region each comprise at least four contiguous cytosines or cytosine derivatives.

8. The complex of claim 1 wherein said complex is produced using two nucleic acid strands each of which comprise at least two cytosine-rich or cytosine derivative-rich regions.

9. The complex of claim 8 wherein each of said cytosine-rich or cytosine derivative-rich regions comprises at least two cytosines or cytosine derivatives.

10. The complex of claim 8 wherein each of said cytosine-rich or cytosine derivative-rich regions comprises at least four contiguous cytosines or cytosine derivatives.

11. The complex of claim 1 wherein at least one of the nucleic acids contained therein is a non-naturally occurring nucleic acid.

12. The complex of claim 2 wherein at least one of the nucleic acids contained therein is a non-naturally occurring nucleic acid.

13. The complex of claim 5 wherein at least one of the nucleic acids contained therein is a non-naturally occurring nucleic acid.

14. The complex of claim 1 wherein said cytosine derivatives comprise substitutions to the sugar phosphate portion of the cytosine structure.

15. A process for producing an "i-motif" nucleic acid complex comprising treating one or more nucleic acid molecules each comprising at least two cytosine-rich or cytosine derivative-rich regions under conditions which provide for the formation of an "i-motif" nucleic acid complex.

16. The process of claim 15 wherein said conditions comprise acidic conditions.

17. The process of claim 15 wherein said cytosine-rich region comprises a telomeric or centromeric sequence.

* * * * *